United States Patent [19]

Thomenius

[11] 4,395,910
[45] Aug. 2, 1983

[54] GEOMETRIC CORRECTION CIRCUIT FOR ULTRASONIC SCAN DISPLAY

[75] Inventor: Kai E. Thomenius, Annandale, N.J.

[73] Assignee: Sonometric Systems, Inc., New York, N.Y.

[21] Appl. No.: 189,730

[22] Filed: Sep. 22, 1980

[51] Int. Cl.³ .............................................. G01N 29/00
[52] U.S. Cl. ...................................... 73/620; 128/660
[58] Field of Search ............................... 128/660–661; 73/610–612, 619–620

[56] References Cited

U.S. PATENT DOCUMENTS 3,913,387 10/1975 Sasaki et al. ........................... 73/611

OTHER PUBLICATIONS

Nakashika, M. et al, "Recent Ultrasonic Tomographic System Sonolayergraph, SSL-31A," Toshiba Review (Intnl. Edition), Jun. 1973, No. 82.

Fuller, G. et al, *Analytic Geometry and Calculus*, Van Nostrand & Co., Princeton, N.J., 1964, pp. 437–441.

*Primary Examiner*—Kyle L. Howell
*Assistant Examiner*—Francis J. Jaworski
*Attorney, Agent, or Firm*—Robert Scobey

[57] ABSTRACT

Circuitry for generating a distortion-free sector display in a cathode ray tube for displaying signals from an ultrasonic transducer moving back and forth in an arcuate path. Sine and cosine beam sweep signals are developed using signals respectively representing the angular position $\theta$ of the transducer on its angular path (representing the sine) and $1-\theta^2/2$ (representing the cosine). A transducer position signal is stored on a relatively large capacitor, and a capacitor of smaller capacitance is used to generate a ramp signal in producing the sine and cosine beam sweep signals.

8 Claims, 5 Drawing Figures

GEOMETRIC CORRECTION CIRCUIT FOR ULTRASONIC SCAN DISPLAY

BACKGROUND AND BRIEF DESCRIPTION OF THE INVENTION

This invention relates to ultrasonic scan and display apparatus, and has particular application to a B-scan unit utilizing an ultrasonic transducer that moves back and forth in an arcuate path.

Ultrasonic scan and display apparatus is known, utilizing an ultrasonic transducer that moves back and forth in an arcuate path at a relatively low frequency, pulsed at a relatively high frequency to generate ultrasonic pulses which enter into an object that is being scanned, e.g., a small organ of the human body or the human eye. Echo pulses from the object scanned are received by the transducer and displayed on a cathode ray tube screen to provide highly useful information regarding the scanned object. Since the cathode ray tube utilizes orthogonal beam deflection, it has been recognized in the past that it is necessary to provide special signals to the beam deflection electrodes in the cathode ray tube to produce a beam trace on the screen of that tube that conforms to the sector scanned by the ultrasonic transducer. Holasek and Sokollu have described in an article published in 1972 Ultrasonics Symposium Proceedings, "Direct Contact, Hand-Held, Diagnostic B-Scanner" a beam deflection circuit for a cathode ray tube utilizing sine and cosine signals, and particularly first-order simulation of sine and cosine functions. Eggleton et al U.S. Pat. No. 3,974,826, issued Aug. 17, 1976, discloses the use of sine and cosine beam deflection signals; in this case, a function generator, such as a Burr Brown sine cosine function generator, is used.

The present invention utilizes sine and cosine signals for appropriate development of a distortion-free sector display in a cathode ray tube incorporating orthogonal beam deflection. The invention recognizes that the sine function may be approximated by the angle itself, that is, sine $\theta \sim \theta$ for small angles (the relative angular position of the ultrasonic transducer in its arcuate path with respect to a reference position), and the following function as representing the cosine function:

$$\text{cosine } \theta \sim 1 - \theta^2/2.$$

Signals representing $\theta$ and $1 - \theta^2/2$ are stored on relatively high capacitance capacitors and then gated onto lower capacitance capacitors as initial values, from which ramp functions are generated to provide the X and Y sweeps of the beam in the cathode ray tube. Elaborate circuitry is avoided, and a simple but highly effective circuit functions to provide appropriate X and Y sweeps to provide a relatively distortion-free sector display in the cathode ray tube.

The invention will be more completely understood by reference to the following detailed description.

BRIEF DESCRIPTION OF THE DRAWINGS

Referring to FIG. 1, an ultrasonic transducer 10 is shown mounted for pivotal movement about an axis 12. The transducer is activated so that it moves back and forth in an arcuate path 14 past an object 16 to be scanned, such as a human eye. Typically, the transducer 10 may move through a total angle that may be anywhere from 18° to 45°. The transducer 10 is typically moved along the arcuate path at a frequency of about 15 Hz. The transducer itself is pulsed at a frequency of approximately 8 kilohertz, to generate a pulsed ultrasonic signal that enters into the object 16 being scanned, from which echo pulses are generated which are received by the ultrasonic transducer and used in the development of a sector display such as that shown in FIG. 2.

In FIG. 2, the sector display is produced by deflecting the cathode ray tube beam in a series of line scans which have been diagrammatically shown and designated 18a, 18b, 18c and 18d. Each of these line scans of the cathode ray tube beam is produced by beam deflection from X-axis and Y-axis beam deflection electrodes. These electrodes produce the conventional orthogonal beam deflection, i.e., the X-axis electrodes deflect the beam horizontally, while the Y-axis electrodes deflect the beam vertically. To produce the actual beam deflection along the lines 18a . . . 18d, the horizontal or X-axis deflection is proportional to the cosine of the angle of the scanning line, while the Y-axis or vertical deflection is proportional to the sine of that angle.

In the past, sine and cosine deflection signals for producing a distortion-free sector display have been generated by using a first-order simulation of sine and cosine functions through direct use of a digital to analogue conversion unit, as described in the Holasek and Sokollu article cited above. Additionally, Eggleton et al, as noted in the patent above, have utilized a Burr Brown sine cosine function generator. The present invention utilizes sine and cosine signals, but generates them through use of a different technique. The circuit of FIG. 5 utilizes sine and cosine approximations in a simple but effective circuit utilizing basically only conventional gates, a multiplier, amplifiers and capacitors for charge storage.

Figure 2:
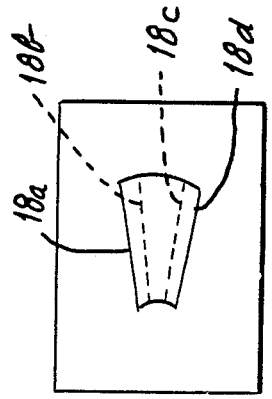
FIG. 2 is a diagrammatic representation of a sector scan display on a cathode ray tube screen developed by signals received from an ultrasonic transducer scanning an object as in FIG. 1.
Figure 4:
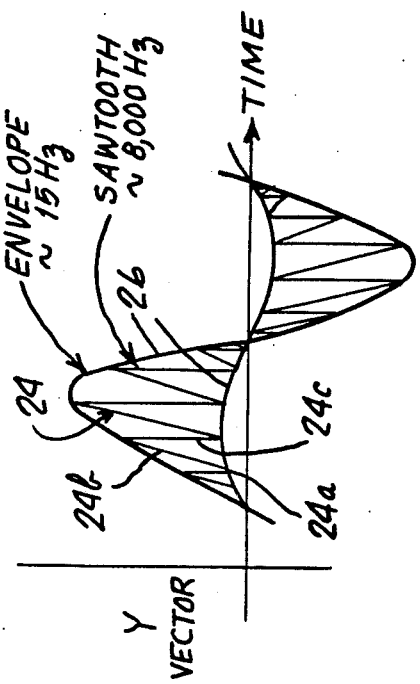
FIG. 4 is a waveform diagram similar to FIG. 3 showing the Y-axis or vertical deflection signal.
Figure 3:
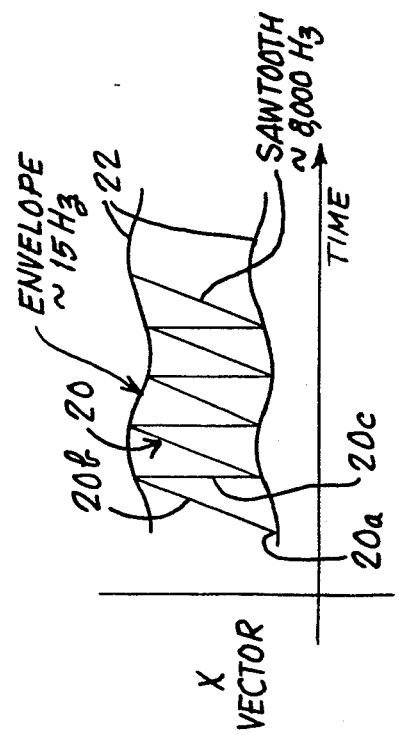
FIG. 3 is a waveform diagram of the signal applied to the X-axis or horizontal deflection plates in a cathode ray tube to produce a sector display as in FIG. 2.
Figure 5:
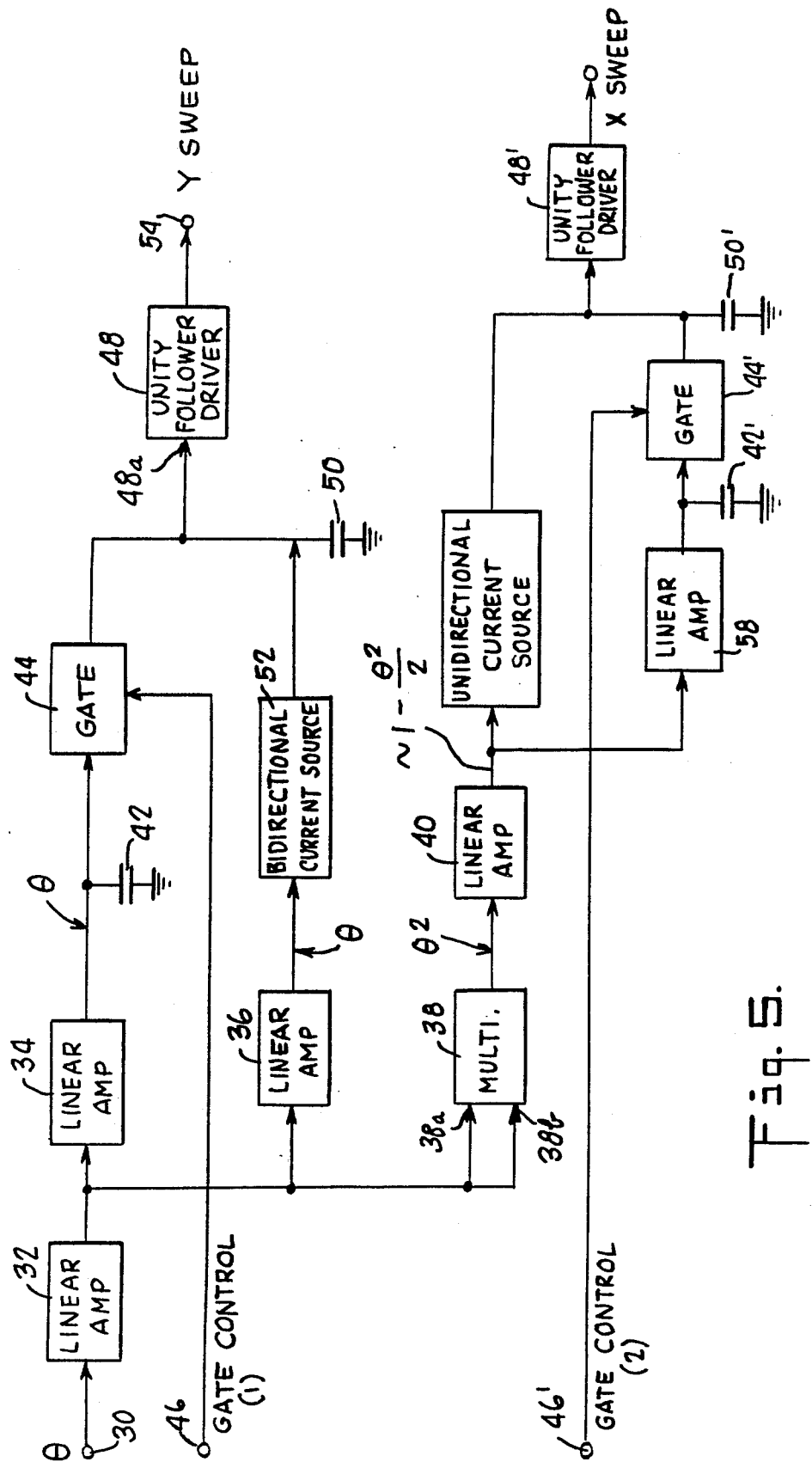
FIG. 5 is a block diagram of a circuit constituting a presently preferred embodiment of the invention for producing the beam deflection signals shown in FIGS. 3 and 4.

Before the circuit of FIG. 5 is described, it is best to refer to FIGS. 3 and 4, which show X-axis and Y-axis waveform diagrams, representing the signals applied to the X-axis and Y-axis deflection plates of the cathode ray tube. The X-axis deflection signal is a saw-tooth 20 varying within an envelope 22. The frequency of the saw-tooth signal 20 is approximately 8 K. Hz., i.e., the rate at which the ultrasonic transducer 10 is pulsed to produce its ultrasonic signal. The waveform envelope 22 represents a sine wave variation of approximately 15 Hz., i.e., the frequency at which the transducer 10 is oscillated in its movement along the arcuate path 14.

The Y-axis deflection signal is shown in FIG. 4. Again, it is a saw-tooth 24 oscillating within envelope 26. The frequency of the saw-tooth waveform 24 is the same as that of the waveform 20 in FIG. 3, while the frequency of the envelope 26 is the same as that of the envelope 22 in FIG. 3. In the case of the waveform of FIG. 4, the envelope 26 has positive and negative excursions since the Y-axis deflection of the beam undergoes both positive and negative trace excursions, while the X-axis beam deflection undergoes only positive trace excursions.

Referring now to FIG. 5, a signal representing $\theta$ is applied to a terminal 30. $\theta$ is the angle of the transducer 10 with respect to a reference position; the angle $\theta$ is shown and so designated in FIG. 1. A signal representing the angle $\theta$ is developed in conventional fashion. For example, a coil (not shown) having a movable core therein (not shown) coupled to the transducer 10 may be used to generate an electrical signal whose amplitude at any time is representative of the angle $\theta$. As noted above, the transducer 10 is generally moved back and forth along the arcuate path 14 at a relatively low frequency, e.g., 15 Hz.

The signal representing $\theta$, as applied to the terminal 30 in FIG. 5, is amplified by a linear amplifier 32, the signal from which is applied to linear amplifiers 34 and 36, as well as to inputs 38a and 38b of multiplier 38. The output signals from the linear amplifiers 34 and 36 are representative of the angle $\theta$, while the output signal from the multiplier 38 represents $\theta^2$ (because the $\theta$ signal is applied to both of the multiplier inputs 38a and 38b). The $\theta$ signal from the multiplier 38 is applied to a linear amplifier 40, the output signal from which is proportional to the function: $1-\theta^2/2$.

At this point it should be noted that the $\theta$ signal from the linear amplifier 34 is used to represent the sine of the angle, since for small angles the sine is approximately equal to the angle itself. The signal from the linear amplifier 40 ($1-\theta^2/2$) represents the cosine of the angle $\theta$. This approximation is valid for relatively small angles $\theta$.

Figure 1:
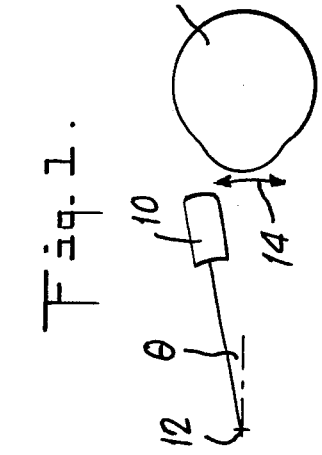
FIG. 1 is a schematic diagram illustrating the movement of an ultrasonic transducer in scanning an object such as a human eye.

Consider first the $\theta$ signal from the linear amplifier 34. It is applied to a capacitor 42 of relatively large capacitance (as will be explained below), e.g., 4.7 uf capacitance. The signal across the capacitor 42 is applied to a gate 44 which is under the control of gating signals from a gate control terminal 46. The gate control terminal 46 is applied with pulse signals at the pulse repetition rate at which the transducer 10 in FIG. 1 is pulsed to generate its ultrasonic pulses that penetrate the object 16 under test. As noted above, these pulses occur at a frequency much greater than the frequency of the $\theta$ signal variation (e.g., 8,000 K. Hz.). The $\theta$ signal applied to the gate 44 is accordingly gated through the gate at the transducer pulsing rate, and the $\theta$ signal is thus applied to input 48a of unity follower driver 48. The input 48a is also coupled to a capacitor 50 and to a bidirectional current source 52.

The $\theta$ signal from the gate 44 is used to establish the initial value 24a of the ramp signal 24 shown in FIG. 4, while the bidirectional current source 52 and capacitor 50 combine to generate the trace (i.e., the sweep) portion 24b of that ramp signal. Specifically, the capacitance of capacitor 50 is much less than that of the capacitor 42 (e.g., 0.001 uf). The gate control signals of the terminal 46 are chosen so that the gate 44 is opened during the time of the trace sweep 20b (FIG. 3) but is closed at all other times. Accordingly, just prior to the commencement of the trace sweep 20b, the gate 44 is closed, and the capacitors 42 and 50 are coupled together. The $\theta$ signal on the capacitor 42 determines the potential applied to the unity follower driver 48. As the trace sweep 24b commences, the gate 44 opens, and the unity follower driver 48 is driven by the signal on capacitor 50, as controlled by the bidirectional current source 52. That current source is applied with a signal representing $\theta$, and hence current flows to the capacitor 50 (or from that capacitor) and the trace portion 24b of the ramp signal generated, driving the unity follower driver 48 to produce the Y-axis or vertical deflection signal at terminal 54 which is coupled to the Y-axis or vertical deflection plates (not shown) of the cathode ray tube. The slope of the ramp signal generated is proportional to $\theta$.

At the end of the trace sweep 24b, the gate 44 is closed by the action of the gate control signal at the terminal 46, and the capacitors 42 and 50 are again coupled together. This coupling action of the capacitors causes the retrace portion 24c of the sweep to occur, causing the capacitor 52 to charge or discharge to the potential across the capacitor 42.

Accordingly, the capacitor 42 and 50, respectively of relatively large and small capacitance, are coupled together and decoupled by the gate 44 at a rate dependent upon the transducer pulsing frequency. The capacitor 42 stores the $\theta$ signal related to the angular position of the transducer in its path, while the capacitor 50 is responsible for producing the trace sweep of the beam in the cathode ray tube. As an example, the trace sweep 24b may persist for approximately 65 micro seconds. The time for the retrace 24c may be less than 1 micro second, and there may be a "dead time" of approximately 60 micro seconds before the commencement of the next trace sweep 24b. These times are dependent upon the circuit parameters in the Y-sweep circuit portion of the circuitry of FIG. 5.

The same techniques are utilized to generate the X-sweep signal. Specifically, the signal from the linear amplifier 40, representing the function $1-\theta^2/2$, is applied to a unidirectional current source 56 as well as to a linear amplifier 58. The linear amplifier 58 feeds a capacitor 42' of relatively large capacitance, e.g., 4.7 uf. It will be noted that the capacitor 42' corresponds to the capacitor 42. The capacitor 50' is of relatively small capacitance, e.g., 0.001 uf, and corresponds to the capacitor 50. Gate 44' couples together the two capacitors at the transducer pulsing frequency, as controlled by a gate control signal applied to gate control terminal 46'. This gate control signal may be the inverse of the cathode ray tube beam blanking signal; if desired the two gate control terminals 46 and 46' may be connected together to receive the same gating input signal. Like the gate 44, the gate 44' couples together the capacitors 42' and 50' at the beginning 20a of the trace sweep 20b in FIG. 3. Thus the cosine approximation signal $1-\theta^2/2$ is applied to unity follower driver 48' corresponding to the driver 48 described above. Once the trace sweep 20b commences, the gate 44' opens, and the unity follower driver generates a ramp signal generated by the action of the unidirectional current source 56 and capacitor 50'. In this case, since the X-axis sweep always increases positively, a unidirectional current source is used rather than a bidirectional current source 52 as in the Y-sweep circuitry.

Retrace of the beam, as represented by retrace sweep 20c in FIG. 3, occurs when the gate 44' is closed to couple together the capacitors 42' and 50', in exactly the same fashion as described above in connection with the Y-axis sweep.

The circuit of FIG. 5 is simply constructed utilizing conventional components, such as integrated circuits, transistors, capacitors and resistors. The linear amplifiers may be integrated circuit operational amplifiers. The multiplier 38 and gate 44 may be integrated circuits, and the gate 44 may be a transistor gate. The current sources 52 and 56, as well as the unity follower drivers 48 and 48' may be integrated circuit operational amplifiers.

It will be appreciated that the circuit of FIG. 5 may be configured in different ways. Further, modifications may be made by those skilled in the art. Thus the invention should be taken to be defined by the following claims.

I claim:

1. In ultrasonic scan and display apparatus utilizing a transducer pulsed at a relatively high frequency and which moves back and forth in an arcuate path at a relatively lower frequency, the improvement for generating a beam deflection signal to produce a sector display in a cathode ray tube comprising first capacitor means of relatively large capacitance for storing a signal related to the angular position of said transducer in said path, second capacitor means of relatively small capacitance for generating a signal producing a trace sweep of the beam in said cathode ray tube, and first gate means for coupling together and decoupling said first and second capacitor means at a rate dependent upon said transducer pulsing frequency.

2. Apparatus according to claim 1, in which said first gate means decouples said first and second capacitor means during trace portions of the sweep of said beam in said cathode ray tube.

3. Apparatus according to claim 2, in which said beam deflection signal produces beam deflection in the direction of an X-axis in said cathode ray tube, and including a source of unidirectional current flow coupled to said second capacitor means.

4. Apparatus according to claim 2, in which said beam deflection signal produces beam deflection in the direction of a Y-axis in said cathode ray tube, and including a source of bidirectional current flow coupled to said second capacitor means.

5. Apparatus according to claim 1, including third capacitor means of relatively large capacitance for storing a signal related to the angular position of said transducer in said path, fourth capacitor means of relatively small capacitance for generating a signal producing a trace sweep of the beam in said cathode ray tube in a direction generally perpendicular to the direction of the trace sweep produced by the signal from the second capacitor means, and second gate means for coupling together and decoupling said third and fourth capacitor means at a rate dependent upon said transducer pulsing frequency.

6. Apparatus according to claim 5, in which said first gate means decouples said first and second capacitor means during trace portions of the sweep of said beam in said cathode ray tube in the direction of an X-axis in said tube, and said second gate means decouples said third and fourth capacitor means during trace portions of the sweep of said beam in said cathode ray tube in the direction of a Y-axis generally perpendicular to said X-axis.

7. Apparatus according to claim 6, including a source of unidirectional current flow coupled to said second capacitor means, and a source of bidirectional current flow coupled to said fourth capacitor means.

8. Apparatus according to claim 7, in which the signal stored by said third capacitor means is generally proportional to $\theta$, and the signal stored by said first capacitor means is generally proportional to $1-\theta^2/2$.

* * * * *